United States Patent
Largeteau et al.

(10) Patent No.: US 10,500,313 B2
(45) Date of Patent: Dec. 10, 2019

(54) METHOD FOR PRODUCING A POROUS MONOLITHIC MATERIAL

(71) Applicants: CENTRE NATIONAL DE LA RECHERCHE SCIENTIFIQUE, Paris (FR); UNIVERSITE DE BORDEAUX, Bordeaux (FR)

(72) Inventors: Alain Largeteau, Cestas (FR); Mythili Prakasam, Talence (FR)

(73) Assignees: CENTRE NATIONAL DE LA RECHERCHE SCIENTIFIQU, Paris (FR); UNIVERSITE DE BORDEAUX, Bordeaux (FR)

( * ) Notice: Subject to any disclaimer, the term of this patent is extended or adjusted under 35 U.S.C. 154(b) by 0 days.

(21) Appl. No.: 15/743,492

(22) PCT Filed: Jul. 15, 2016

(86) PCT No.: PCT/FR2016/051821
§ 371 (c)(1),
(2) Date: Jan. 10, 2018

(87) PCT Pub. No.: WO2017/013339
PCT Pub. Date: Jan. 26, 2017

(65) Prior Publication Data
US 2018/0200409 A1 Jul. 19, 2018

(30) Foreign Application Priority Data
Jul. 17, 2015 (FR) ....................... 15 56771

(51) Int. Cl.
*A61L 27/56* (2006.01)
*C04B 30/00* (2006.01)
*A61L 27/12* (2006.01)
*A61L 27/02* (2006.01)
*A61L 27/22* (2006.01)
*A61L 27/24* (2006.01)
*C01B 25/32* (2006.01)
*C01F 7/02* (2006.01)
*C01G 23/08* (2006.01)
*C01G 25/00* (2006.01)
*C01G 25/02* (2006.01)
*C04B 111/00* (2006.01)

(52) U.S. Cl.
CPC ............. *A61L 27/56* (2013.01); *A61L 27/025* (2013.01); *A61L 27/12* (2013.01); *A61L 27/222* (2013.01); *A61L 27/24* (2013.01); *C01B 25/327* (2013.01); *C01F 7/021* (2013.01); *C01G 23/08* (2013.01); *C01G 25/006* (2013.01); *C01G 25/02* (2013.01); *C04B 30/00* (2013.01); *A61L 2430/02* (2013.01); *C04B 2111/0081* (2013.01); *C04B 2111/00836* (2013.01); *C04B 2111/00844* (2013.01)

(58) Field of Classification Search
None
See application file for complete search history.

(56) References Cited

U.S. PATENT DOCUMENTS

| 2010/0167020 | A1* | 7/2010 | Jones | A61F 2/30942 |
| | | | | 428/195.1 |
| 2014/0141224 | A1* | 5/2014 | Pasquali | C01B 31/00 |
| | | | | 428/219 |
| 2014/0314824 | A1 | 10/2014 | Kim et al. | |
| 2017/0100857 | A1* | 4/2017 | Bai | B29C 39/38 |

FOREIGN PATENT DOCUMENTS

| CN | 103599561 | 8/2015 | | |
| EP | 1500405 | 1/2005 | | |
| EP | 1566186 | 8/2005 | | |
| EP | 1964583 | 9/2008 | | |
| JP | 2009-254547 | * 11/2009 | ............... | A61F 2/28 |
| JP | 2009254547 | 11/2009 | | |
| KR | 20110088903 | 8/2011 | | |
| LV | 14492 | 3/2012 | | |

OTHER PUBLICATIONS

French Search Report dated May 1, 2016 in corresponding French Application No. 1556771.

* cited by examiner

*Primary Examiner* — Brian Gulledge
(74) *Attorney, Agent, or Firm* — Young & Thompson

(57) ABSTRACT

Disclosed is a method for producing a porous monolithic material from at least one powder, preferably mineral, the method including at least one step of low-temperature compression of a mixture based on powder and at least one solvent, preferably water. The materials produced by the method have improved mechanical properties compared to the prior art materials. The materials for medical application, such as hydroxyapatite, also have improved biocompatibility compared to the prior art materials. Also disclosed are materials produced by the method.

17 Claims, 6 Drawing Sheets

METHOD FOR PRODUCING A POROUS MONOLITHIC MATERIAL

Figure 1:
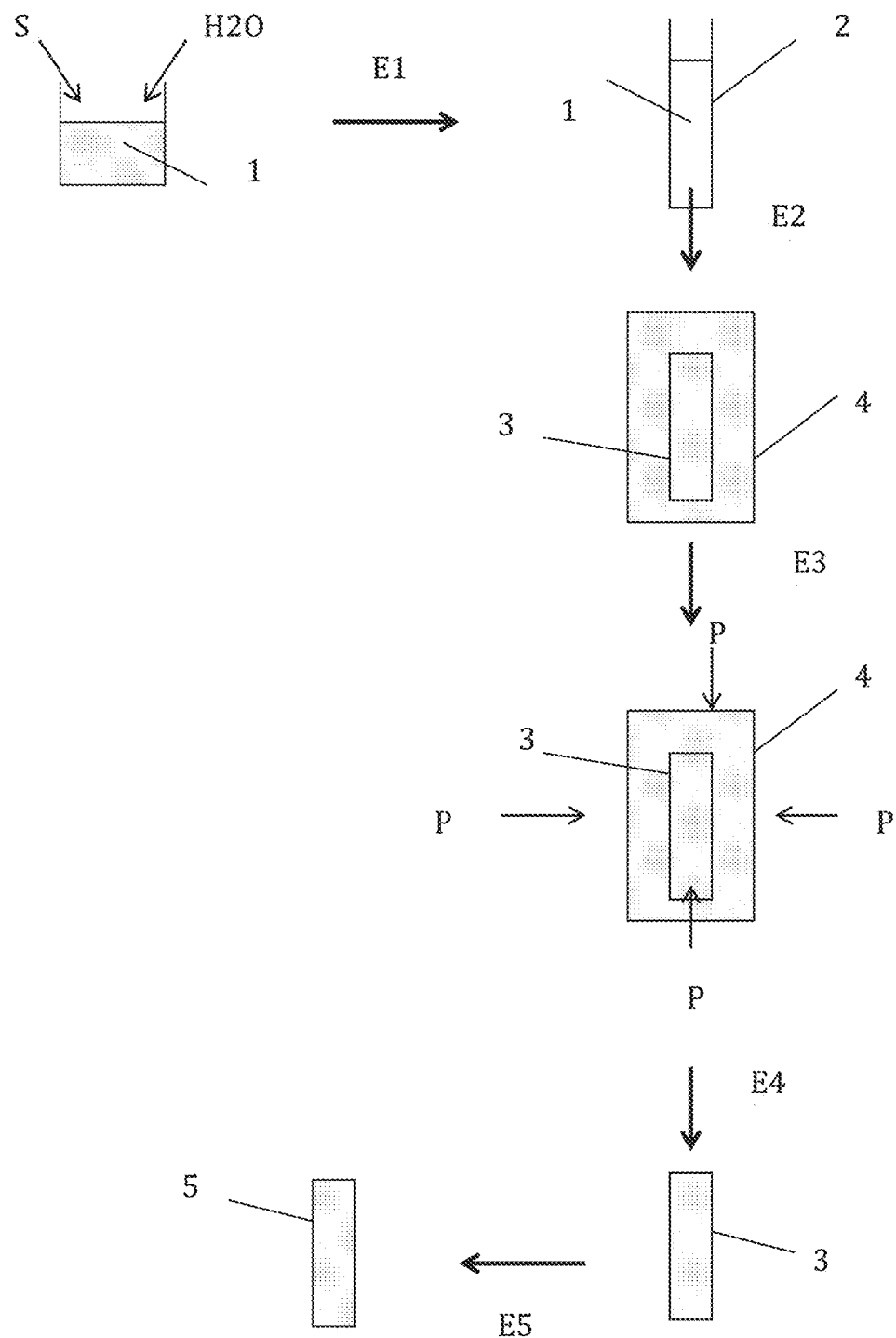

The present invention relates to a method for producing a porous monolithic material from at least one powder, preferably mineral, this method comprising at least one step of low-temperature compression of a mixture based on mineral powder and at least one solvent, preferably water. The materials obtained by this method have improved mechanical properties with respect to the prior art materials. In the case of materials for medical application, such as hydroxyapatite for example, they also have improved biocompatibility with respect to the prior art materials. The invention also relates to the materials obtained by this method.

STATE OF THE PRIOR ART

The production of porous monolithic materials based on alkali or alkaline earth metals, such as hydroxyapatite, titanium dioxide, alumina or zirconia, for example, can currently be carried out using various methods.

It is possible to start from a mineral powder, to which a sintering technique is applied, which consists of heating to a high temperature in order to stiffen the initial granular structure. This technique, which includes different variants (conventional sintering or free sintering, hot press sintering, hot isostatic press sintering), is not without drawbacks. Heating to high temperature leads to a change in the chemical structure of the mineral raw material, in particular partial removal of the oxygen atoms and hydroxides. A hydroxyapatite subjected to such treatment has lower biocompatibility than the initial hydroxyapatite. A titanium dioxide heated beyond 500° C. is no longer biocompatible, as the anatase form, the only biocompatible form, is degraded at this temperature. Alumina $Al_2O_3$ and zirconia $ZrO_2$ also display structural transitions at high temperature and can lose their biocompatibility through the application of such treatment. Another disadvantage of this method is that no organic raw material can be incorporated into the mineral powder before sintering, as it would be decomposed by this heat treatment. Organic raw material, such as active pharmaceutical ingredients, can therefore only be incorporated after formation of the monolith, which increases the number of steps and makes it more difficult to obtain a homogeneous material.

Techniques other than sintering exist for producing porous monolithic materials based on mineral raw material. Additive manufacturing (three-dimensional printing) is a technique that requires localized heating with a laser, which equates to heating to a high temperature. This is in particular the case in selective laser fusion and selective laser sintering methods. A slurry containing the mineral raw material and a chemical additive acting as a pore-forming material for the formation of pores can also be cast in a mould. The pore-forming material is then removed in the form of gas by heating or remains in the material, if no heating takes place, in the form of "sponge". The structure formed by this additive gives the material flexible but not stiff mechanical strength. The production of porous monoliths is also known by casting a slurry containing water in a cold mould (at negative temperature). The water contained in the slurry forms ice crystals that are then removed, by lyophilisation for example. Such a method produces a very friable material. As a general rule, it is necessary to add a gelatinising agent to give such a material mechanical strength, and the strength thereof remains fairly low nevertheless. It can even be sintered subsequently to improve its strength. It might be that some elements of the slurry remaining in the end material are not biocompatible.

It is known to subject a powder to isostatic pressure at ambient temperature in such a way as to form a monolith. This then produces a dense but non-porous material.

Application KR20110088903 describes a method for producing a porous material based on hydroxyapatite, this method comprising the formation of an alcohol-based slurry that is frozen, the removal of the pore-forming alcoholic solution and then the sintering of the material. The disadvantages of this method are in particular the use of a sintering step that modifies the chemical structure of the material.

Application CN103599561 describes a composite material, which can be used as a bone replacement, based on magnesium and hydroxyapatite, the method for producing this material comprising the mixing and then the cold pressing of the mixture in a mould and the sintering of the material.

Application LV14492 describes a porous material based on hydroxyapatite provided with a bimodal pore distribution, this material being able to be used as a bone replacement material. The production method utilizes ammonium bicarbonate as a pore-forming agent. Such a material has unsatisfactory mechanical properties.

Application US2014/0314824 describes a method for producing a biocompatible porous substrate that can be used for tissue culture, based on chitosan, hydroxyapatite and amylopectin. The production of the material includes dissolving the chitosan in a solution of acetic acid, adding hydroxyapatite and then amylopectin, and finally freezing the solution, neutralising it with an alkaline aqueous solution and washing and drying the material. This method provides a material the mechanical strength of which is not entirely satisfactory.

Document JP2009-254547 describes a method for producing a bone regeneration material from an octocalcic phosphate, a hydroxyapatite precursor. This material is mixed with a water-soluble polymer or a polysaccharide such as sodium alginate and the mixture is subjected to treatment consisting of a pressure increase from $4.1 \times 10^{-3}$ MPa to $3.7 \times 10^{-2}$ MPa. Heat treatment is necessary to sterilize the material.

Document US2014/0141224 describes a material of the carbon foam type prepared from a carbonaceous material, such as carbon nanotubes, that is dissolved in an acidic medium, the solution is moulded and the carbon source is coagulated. The coagulated material can be lyophilized or dried.

Document EP 1 566 186 describes a porous coagulated apatite/collagen material. This material is prepared from a mixture of an apatite/collagen composite and collagen. This mixture is gelatinized then lyophilized and cross-linked.

Document EP 1 964 583 describes a method for producing a composite collagen/hydroxyapatite material, comprising the formation of a homogeneous suspension of collagen and hydroxyapatite in an acidic solution, the lyophilisation of the solution and optionally the cross-linking of the material.

Document EP 1 500 405 describes a method for producing porous composite materials from a calcium salt and collagen, comprising the freezing of a complex formed from a calcium salt and at least partially gelatinized collagen, and the lyophilisation thereof.

None of these methods results in a material having both satisfactory porosity and satisfactory mechanical strength.

The aim of the invention is to overcome the problems encountered with the prior art materials. In particular, the development of a reliable and reproducible method has been sought that makes it possible, from a powder, in particular a selected mineral powder, to form a monolith with the same chemical composition, without degradation of the initial chemical structure, this monolithic material having good mechanical strength properties. The development has also been sought of a method that makes it possible to incorporate optional organic components into the material from the first steps of its production, so that the monolithic material has a homogeneous composition. The development has therefore been sought of a production method that does not degrade the organic molecules, in particular that does not comprise a step of heating to high temperatures, such as a sintering step for example.

SUMMARY OF THE INVENTION

The invention relates to a method for producing a porous monolithic material, this method comprising at least the following steps:
  (a) Supplying at least one mineral or organic powder,
  (b) Preparing a mixture comprising at least the powder of step (a) and at least one solvent, preferably water,
  (c) Packing the mixture of step (b) in sealed packaging made from an elastically deformable material in order to form a sample,
  (d) Applying to the sample of step (c) a pressure greater than or equal to 50 MPa at a temperature at which the solvent is in solid form,
  (e) Returning to atmospheric pressure,
  (f) Opening the packaging and recovering the material,
  (g) Removing the solvent at a temperature at which the solvent is in solid form.

A further aim of the invention is a porous monolithic material that can be obtained by the method of the invention.

According to a preferred embodiment, the powder is selected from mineral or inorganic powders and preferably from: metals, in particular alkali and alkaline earth metals, transition metals, their salts and derivatives, in particular oxides, hydroxides, phosphate and carbonate salts, borides, carbides, nitrides; ceramics and composite materials.

According to a preferred embodiment, the powder is mineral or inorganic and is selected from: hydroxyapatite, alumina, titanium dioxide, zirconia, Yttria-Stabilized Zirconia (YSZ) and Magnesia Partially Stabilized Zirconia (PSZ).

According to a preferred embodiment, the mixture of step (b) comprises at least one organic component, preferably selected from: a therapeutic active ingredient; peptides; proteins; coagulants; markers; growth factors; natural or synthetic polymers; dopants for electronics; electrically conductive polymers; chemical sensors; a cross-linking agent; a water-miscible solvent.

According to a preferred embodiment, the mixture comprises 50 to 95% by weight of powder, preferably mineral or inorganic powder, with respect to the total weight of the mixture.

According to a preferred embodiment, the mixture comprises 60 to 90% by weight of powder, preferably mineral or inorganic powder, with respect to the total weight of the mixture.

According to a preferred embodiment, the pressure applied in step (d) is an isostatic pressure.

According to a preferred embodiment, step (d) comprises at least the following sub-steps:
  (d1) Conditioning the sample at atmospheric pressure and at a temperature selected so that the solvent, preferably water, is in solid form,
  (d2) Applying a pressure greater than or equal to 50 MPa at a temperature selected so that the solvent, preferably water, is in solid form.

According to a preferred embodiment, step (d) comprises at least conditioning at a temperature of between −5° C. and −60° C. and at a pressure of between 50 MPa and 700 MPa.

According to a preferred embodiment, step (d) comprises at least conditioning at a temperature of between −5° C. and −60° C. and at a pressure of between 100 MPa and 600 MPa.

According to a preferred embodiment, the solvent is water.

According to a preferred embodiment, the removal of the water in step (g) is carried out by lyophilisation.

According to a preferred embodiment, the material of the invention is based on at least one material selected from metals, metal salts, metal derivatives, ceramics and composite materials, preferably based on a material selected from hydroxyapatite, alumina, zirconia or $TiO_2$.

The method of the invention makes it possible, on the basis of a mineral or organic material in powder form, to obtain a monolith having a structure and chemical composition that are unchanged with respect to the initial powder, but high cohesion and mechanical strength.

The method of the invention makes it possible to obtain a porous monolithic material having substantially homogeneous porosity.

The method of the invention makes it possible to obtain monolithic materials based on a mineral material and comprising homogeneously dispersed organic components.

The method of the invention makes it possible to easily obtain a monolithic material in the desired shape.

The method of the invention is simple to implement and reproducible.

The method of the invention makes it possible to prevent the development of microbial contamination, in particular bacterial, during production.

The properties of the monolithic material (porosity, mechanical strength) can be modulated by means of controlling the parameters of the method (quantity of solvent, in particular water, pressure, temperature, duration of application of pressure).

The porous monolithic material obtained by the method of the invention differs from the prior art materials in its structure and chemical composition, which are unchanged with respect to the initial material, its mechanical strength and its substantially homogeneous porosity. In particular, the porosity is distributed substantially evenly throughout the volume of the material and the size of the pores is substantially homogeneous throughout the material.

FIGURES

FIG. 1: Diagrammatic representation of the steps of the method according to the invention.

Figure 2:
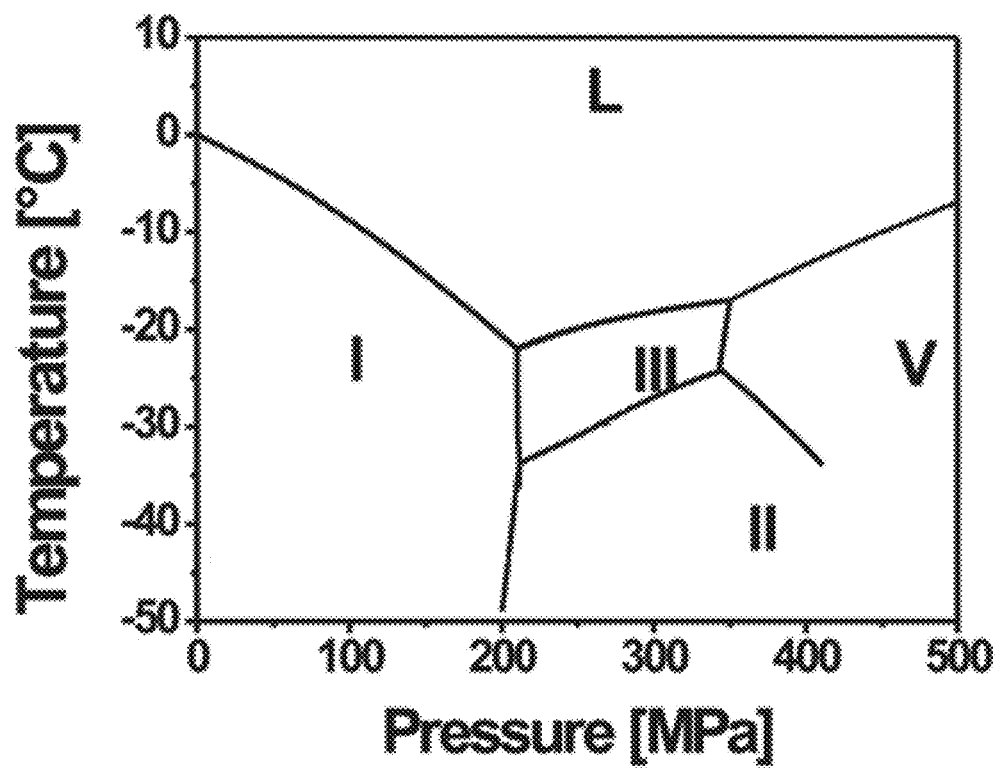

FIG. 2: Phase diagram of water.

Figure 3:
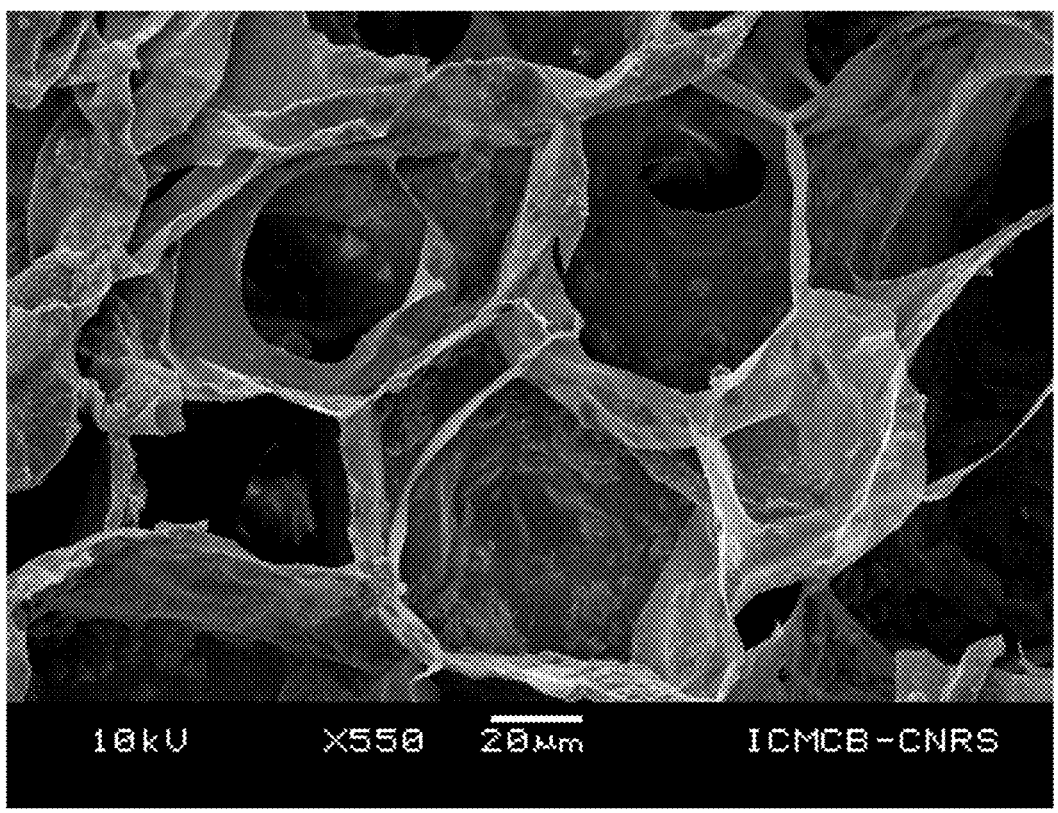

FIG. 3: Microstructure of a material obtained by cold isostatic compression, based on HAp, gelatin and 40% water by weight, viewed by scanning electron microscopy (SEM).

Figure 4:
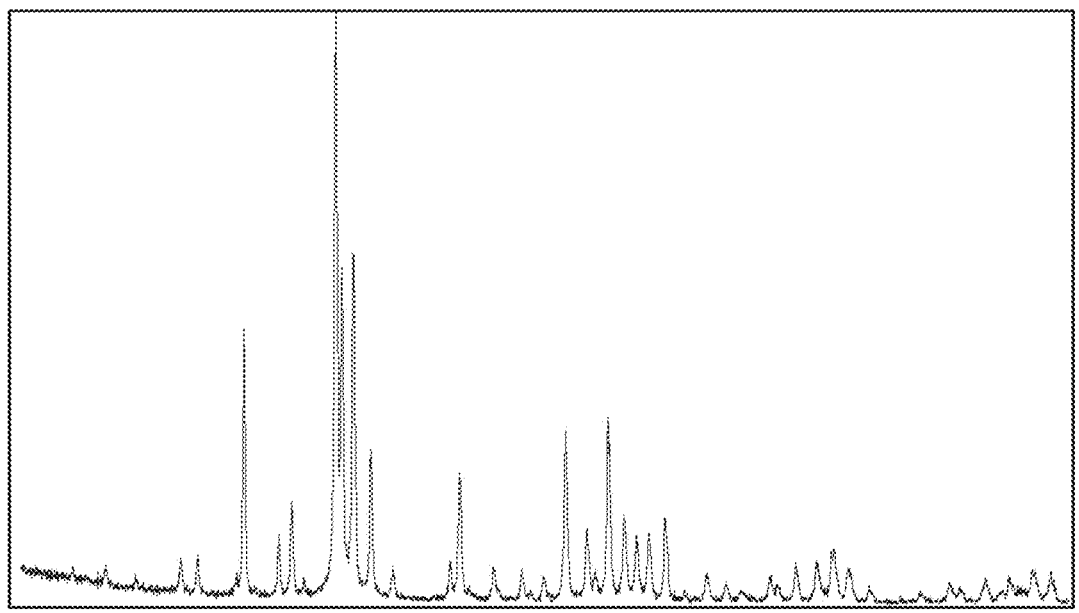

FIG. 4: X-ray diffractogram of the material based on HAp, gelatin and 40% water, obtained by cold isostatic compression.

Figure 5A:
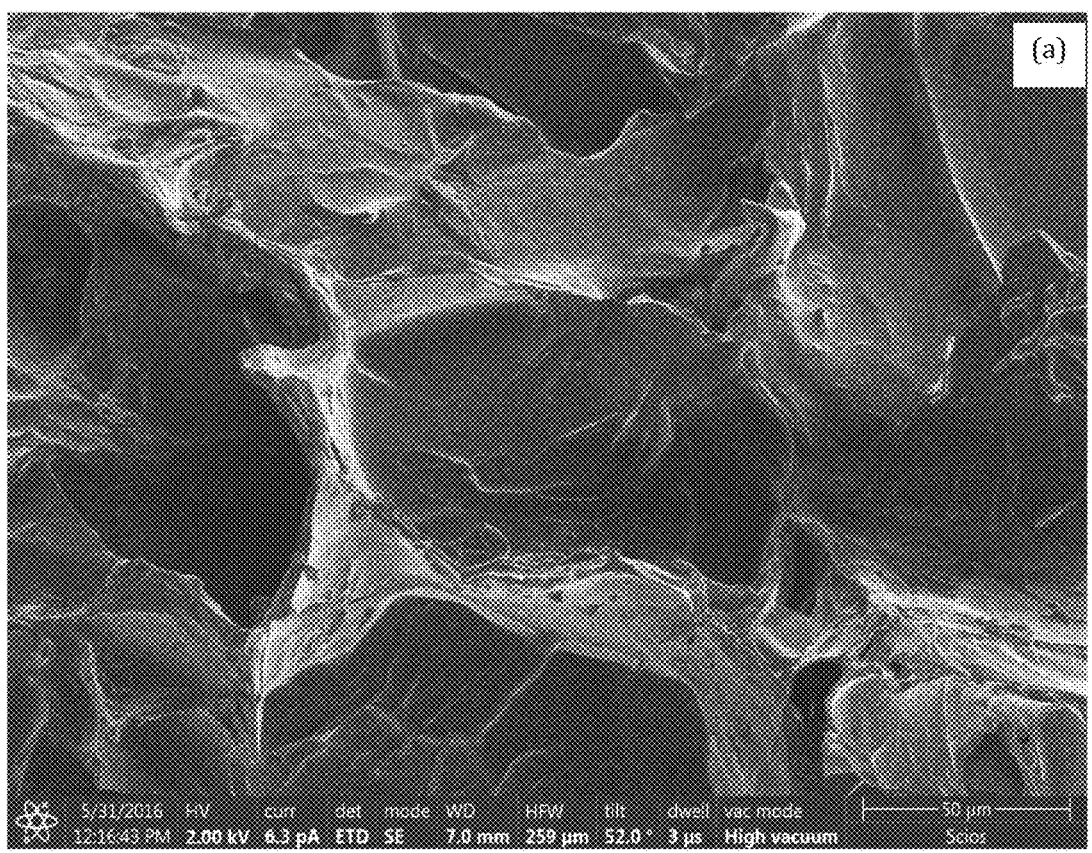

FIG. 5a: X-ray diffractogram of the material based on 80% HAp and 20% water (example 1.1b), obtained by cold isostatic compression.

Figure 5B:
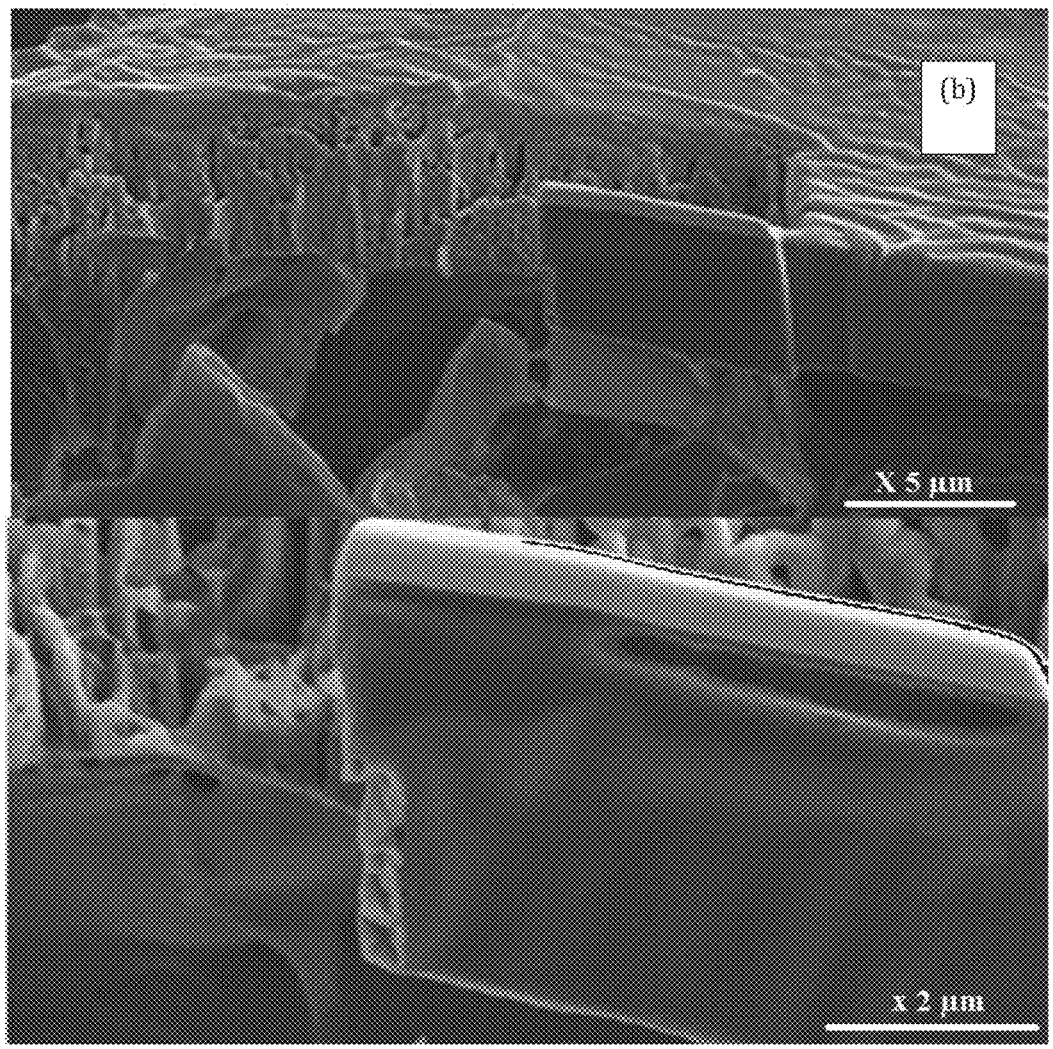

FIG. 5b: X-ray microtomography photo of the material based on 80% HAp and 20% water (example 1.1b), obtained by cold isostatic compression.

DETAILED DESCRIPTION

The invention relates to a method for producing a porous monolithic material from at least one mineral or organic powder, this method comprising the formation of a mixture comprising at least the powder and at least one solvent, preferably water for applications requiring biocompatibility, and optionally organic components. The mixture is placed in sealed plastic packaging and cooled so that the solvent present in the mixture forms crystals, in particular so that the water used as a solvent forms ice crystals. The frozen material is then subjected to high pressure in such a way as to consolidate the structure and form a monolith from the grains of powder, in particular mineral powder. After a return to atmospheric pressure and ambient temperature, the packaging is opened and the material is recovered and then the solvent, in particular water, is removed under conditions making it possible to prevent damage to the chemical structure of the monolith and/or the optional organic components. In particular, the solvent is preferably removed at a temperature at which it is in solid form.

The method of the invention consists of consolidating a sample, which is a mixture containing powder, for example hydroxyapatite (HAp), in the presence of a certain proportion of solvent, in particular water, in the form of crystals. Densification takes place in an isostatic environment and with a pressure of up to 800 MPa transmitted by a pressure-transmitting fluid through the flexible packaging containing the sample. The packaging makes it possible to handle the sample easily and prevents contamination by the pressure-transmitting fluid.

The Mineral or Organic Powder:

The method of the invention can be implemented using any material available in powder form, and in particular using a powder of a mineral or organic material. The powder of the initial material must be insoluble in the solvent, in particular in water when it is used as solvent. There may be mentioned as examples of usable materials: metals, in particular alkali and alkaline earth metals, transition metals, their salts and derivatives, in particular oxides, hydroxides, phosphate and carbonate salts, borides, carbides, nitrides; they also include ceramics and composite materials. Carbon powders may also be mentioned. Among the organic powders that can be used in the method of the invention, polymer powders may be mentioned in particular.

Advantageously, the method of the invention applies to mineral or inorganic powders.

The method is of particular interest for the production of monoliths from raw materials such as:
- calcium phosphates, in particular hydroxyapatite (HA): $Ca_{10}(PO4)_6(OH)_2$, beta-tricalcium phosphate (β-TCP): $Ca_3(PO_4)_2$, biphasic calcium phosphates (BCP) resulting from the mixing of HA and β-TCP, oxyapatite, tetracalcium phosphate, calcium pyrophosphate and fluoroapatite; of these compounds, hydroxyapatite and BCP, which particularly promote bone reconstruction, are preferred;
- ceramics, in particular alumina ($Al_2O_3$), zirconia (ZrO2), Yttria-Stabilized Zirconia (YSZ) or Magnesia Partially Stabilized Zirconia (PSZ), magnesia (MgO), boron nitride (BN), silicon nitride ($Si_3N_4$), silicon carbide (SiC), aluminium titanate ($Al_2TiO_5$) and aluminium nitride (AlN);
- titanium derivatives, in particular titanium dioxide;
- quartz or silicon dioxide ($SiO_2$), optionally comprising traces of elements such as Al, Li, B, Fe, Mg, Ca, Ti, Rb, Na and OH;

The powder utilized in the method as the initial material can be composed of a single material (for example hydroxyapatite) or it can be composed of a mixture of materials (for example BCP).

The initial material powder preferably has a particle size less than or equal to 1 μm. Preferably, it has a particle size of between 0.1 and 500 nm, advantageously 0.5 and 100 nm.

The Powder and Solvent Mixture:

The solvent can be any solvent capable of solidifying under selected pressure and temperature conditions. Advantageously, the solvent is water, the conditions for the formation of ice crystals and the evaporation conditions of which can easily be controlled. Furthermore, water has the advantage of being compatible with applications to biomaterials.

The powder, in particular the mineral or inorganic powder, must not be soluble in the solvent, in particular in water.

The mixture of powder and solvent, in particular water, must comprise sufficient solvent to form, after cooling of the mixture, a network of crystals, in particular ice crystals, which is the source of the porosity in the monolithic material. Controlling the quantity of solvent, in particular the quantity of water, allows control of the morphology of the end material; in particular, the quantity of solvent influences the pore volume of the end material. The mixture must comprise sufficient powder to form a homogeneous paste. Too large a quantity of solvent, in particular water, does not allow the formation of a monolithic material as the particles are spaced too far apart to permit this formation. The quantity of powder incorporated into the mixture also depends on the density of the powder.

The mixture of powder and solvent, in particular water, advantageously comprises 50 to 95%, preferably 60 to 90%, by weight of powder with respect to the total weight of the mixture.

The mixture of powder and solvent, in particular water, can also comprise other organic or inorganic components, such as for example:
- in the case of bone replacement materials: therapeutic active ingredients; peptides; proteins; coagulants, such as for example thrombin or calcium chloride; markers, in particular fluorescent markers; growth factors; natural or synthetic polymers such as for example gelatin, collagen, hyaluronic acid, chitosan, keratin, alginate, fibronectin, fibrinogen, polyglycolic acid (PGA), poly-lactic acid (PLA) and poly(lactic-co-glycolic) acid (PLGA) copolymers;
- in the case of materials for application in electronics: dopants; electrically conductive polymers;
- in the case of materials for producing chemical sensors: molecules capable of reacting with the target molecule;
- a cross-linking agent that makes it possible to consolidate the structure of the material by the creation of chemical cross-linking, such as for example sulphur, a diacid, an anhydride and a polyamine;
- water-miscible solvents, provided that they do not prevent the solidification of water at low temperature.

When an additional organic or mineral material is present in the mixture, it advantageously represents up to 10% by weight with respect to the total weight of the mixture.

Preferably, organic or mineral additional raw materials, soluble in the solvent selected, are used in order to facilitate the production of a homogeneous material. When, preferentially, the solvent is water, water-soluble raw materials are selected.

The Packaging of the Initial Material

The method of the invention is based on the selection of a packaging material that can be closed in a sealed manner. To this end, a heat-sealable material such as a thermoplastic is advantageously selected. The material constituting the packaging must be elastically deformable; in particular, it must be elastically deformable at very low (negative) temperatures such as temperatures of around −40° C. to −60° C.

Among the packaging materials capable of being used in the method of the invention, there may be mentioned in particular polyethylene (PE) or silicones. An entirely different film composed of one or more layers of materials of a different chemical nature or not capable of being heat sealed and elastically deformable at the temperatures and pressures implemented in the method can also be utilized. The shape of the packaging makes it possible to control the shape of the desired end material.

The Steps of the Method:

The method of the invention is illustrated diagrammatically in FIG. 1, with reference to which:

The solid powder (S) and the water, together with any additives (not shown) are prepared so as to form a homogeneous mixture 1. The mixture 1 is placed in a pouch 2 made from an elastically deformable heat-sealable material (step E1). The mixture 1 packed in its sealed packaging so as to form a sample 3 is placed in a negative temperature thermostatic bath 4 at atmospheric pressure (optional step E2). The sample 3 is then subjected to an increase in pressure P under isostatic conditions and at a temperature at which the water, contained in the initial mixture as a solvent, is solid. The isostatic conditions are obtained by placing the packaged sample 3 in a pressure-transmitting environment (cryogenic environment 4), in particular a pressure-transmitting fluid, such as for example ethylene glycol or a silicone oil. The sample 3 is then returned to ambient temperature and pressure conditions (step E4). The polymer packaging material is removed, the material is then lyophilized (step E5) so as to remove the water quickly and obtain the dehydrated, consolidated material 5.

Advantageously, the sample is subjected to a pressure greater than or equal to 100 MPa for at least 5 mins.

The originality of this method lies in the application of an isostatic pressure P when the sample contained in its packaging is immersed in the pressure-transmitting environment, which is at a sufficiently low negative temperature (as low as −40° C. or −60° C.) to transform the water contained in the sample into ice crystals. These ice crystals transform into a solid network (Template) that acts as a substrate around which the particles forming the powder (HAp for example) are compressed.

It is also possible to modify the morphology of the ice crystals formed in the tube by means of an external temperature gradient, to the cryogenic temperature, and then by applying further pressure in addition to the high pressure, which contributes to improving the mechanical strength. In addition, the morphology of the ice crystal can be modified by means of the pressure range used.

The sample can be subjected to several successive steps of application of an isostatic pressure, varying the temperature and pressure parameters depending on the water phase diagram, so that the water that it contains is solid. A specific feature of the water phase diagram shows that defrosting is possible in a range that can be as low as −20° C. at 200 MPa. This range must be avoided when the ice crystals are formed. The formation of the crystals is possible for example by keeping the pouch in the cooled bath for a few minutes and then following this with the application of pressure or, for example, by applying the pressure as soon as the pouch is immersed in the bath, or it is also possible to start the cycle from the liquid range under pressure. It is thus possible by means of parameters P, T and t to follow different paths on the phase diagram to vary the size of the ice crystals. The water phase diagram (FIG. 2) shows the existence of several crystallographic varieties of the ice crystals, differentiated by their density. Only the ice I is less dense than water; all of the other varieties are denser than that of type I.

The pressure increase can be obtained for example by placing the sample in a chamber that is in turn placed in a cryogenic environment.

When the pressure is released and then the sample is removed from the bath still at a very low negative temperature, this sample returns to ambient temperature and the ice crystals return to liquid form; otherwise, the sample is kept in a freezer before being lyophilized. After opening of the package, the water is removed so as to obtain a dehydrated product. Preferably, this dehydration is achieved by means of (vacuum) lyophilisation, which allows the transformation of the water from the solid state to the vapour state without passing through the liquid phase, by sublimation in preference to fusion. Thus the soluble materials in the water, such as therapeutic active ingredients, are not affected by this step, the removal of the water is quick and efficient, and potential bacterial contamination of the material is avoided.

After removal of the water, under the effect of the compression of the particles around the solid network (Template) of ice crystals, a porous monolithic consolidated structure is obtained. This Template based on crystallized water in the form of ice acts as a clean, natural pore-forming agent.

The part recovered is therefore rigid and has a porous microstructure the pore size of which depends on the size of the ice crystals previously formed. The proportion of pores by volume of the end part depends on the volume ratio between the liquid phase (water) and the solid phase. The porous structure is continuous, which then allows the removal of the aqueous phase.

The size and shape of the ice crystal depend on the temperature cycle under pressure (temperature/time/pressure) undergone in the water phase diagram (P, T). The size of the ice crystal depends on the residence time in the negative temperature bath before the pressure increase, as the longer this time, the greater the growth of the crystals.

According to a first embodiment, in a first step the sample placed in its packaging is conditioned at a negative temperature and atmospheric pressure so that the water contained in the sample solidifies. Then, according to this embodiment, the frozen sample is placed in an isostatic press, still at negative temperature, the temperature being adjusted depending on the pressure selected, so that the water is still in solid form.

According to a second embodiment, the sample placed in its package is subjected to a pressure increase and a negative temperature such that the water remains liquid. Then the pressure is increased and/or the temperature is decreased so as to form ice crystals.

This option given by the phase diagram is based on the fact that water is in liquid form at a negative temperature (for example −20° C.) at high pressure (for example 200 MPa). This specific feature makes it possible to remove any germination/growth of the ice crystals in the sample. It is thus possible to promote prolific and therefore very fine germination of ice crystals that can then be used to obtain a consolidated part with a very fine porous structure provided that the temperature/pressure pair is modified with respect to the initial (T/P) pair (for example −20° C./200 MPa).

It must be noted that the isostatic pressure makes it possible to obtain a monolith having an equiaxed porous structure, thus without any particular orientation. However, it is possible to have an oriented structure in the case of a temperature gradient applied during the formation of the ice crystals.

The parameters of the method are adjusted, such as the temperature of the bath forming the pressure-transmitting environment, the dwell time before application of pressure, the compression speed, the pressure level applied, the pressure application duration and the decompression speed, so that the densification is sufficient to obtain a part having the desired consolidation. The hardness of the material is a factor to consider: the harder the initial granular material, the higher the pressure that must be applied to form a monolithic structure.

Preferably, step (d) of the method comprises at least one conditioning at a temperature of between −5° C. and −60° C. and a pressure of between 50 MPa and 700 MPa, preferably 100 MPa and 600 MPa.

Porous Monolithic Material:

The porous monolithic material obtained by the method of the invention has innovative properties with respect to the prior art materials.

The crystallographic structure and chemical composition are unchanged with respect to the initial mineral or inorganic material because there is no heating, the mechanical strength and rigidity are significantly greater in comparison with the same unheated material, the rigidity is greater, the porosity of the material is at least as homogeneous as that obtained by sintering methods or liquid methods using a pore-forming agent.

X-ray diffraction can be used to observe the preservation of the crystallographic structure.

Electron microscopy can be used to observe the morphology of the porosity.

The hardness is evaluated by an indentation testing machine.

The invention relates in particular to a porous monolith based on at least one material selected from metals, metal derivatives, metal oxides, metal hydroxides, ceramics and composites the chemical structure of which is that of metals, metal derivatives, metal oxides, metal hydroxides, ceramics and granular composites. Unlike the prior art materials, the structure and chemical composition of the material of the invention are not modified by the consolidation method.

The invention relates in particular to a porous monolith essentially constituted by a material selected from metals, metal derivatives, metal oxides, metal hydroxides, ceramics, composites and mixtures thereof. Such a material can optionally comprise one or more organic components such as therapeutic active ingredients and dopants. Unlike the porous monoliths of the prior art, the material of the invention does not require the addition of gelatinising materials or thickening or viscosifying polymers to have satisfactory mechanical strength.

Advantageously, the metals, metal derivatives, metal oxides, metal hydroxides, ceramics and composites represent at least 90% by weight, preferably at least 95%, more preferably at least 98% by weight with respect to the total weight of the porous monolith of the invention.

Advantageously, the gelatinising materials or the thickening or viscosifying polymers represent less than 10% by weight, preferably less than 5% and more preferably less than 2% by weight with respect to the total weight of the porous monolith of the invention.

The invention relates in particular to a porous monolith based on hydroxyapatite the chemical structure of which is that of granular hydroxyapatite, i.e. $Ca_{10}(PO4)_6(OH)_2$.

The invention relates in particular to a porous monolith based on BCP, the chemical structure of which is that of granular BCP, i.e. a mixture of HA: $Ca_{10}(PO4)_6(OH)_2$ and β-TCP: $Ca_3(PO_4)_2$.

The invention relates in particular to a porous monolith based on alumina, the chemical structure of which is that of granular alumina, i.e. $Al_2O_3$.

The invention relates in particular to a porous monolith based on zirconia, the chemical structure of which is that of granular zirconia, i.e. $ZrO_2$.

The invention relates in particular to a porous monolith based on $TiO_2$, the chemical structure of which is that of granular anatase titanium dioxide.

Uses of the porous monolithic materials: The monolithic materials of the invention have applications in a number of fields:

- as a bone or tooth replacement material, as a rigid and porous prosthesis, for bone or tooth regeneration, in the case of materials based on hydroxyapatite;
- for applications in anode plates, nanoelectronic devices, high-density storage peripherals, sensitive chemical sensors and for functional nanomaterials in the case of porous alumina;
- for applications in oxide fuel cells, ceramic filters, thermal barriers, dental applications and biological materials in the case of porous zirconia;
- for photonic catalyst applications in the case of porous titanium oxide;
- to obtain fine layers of porous titanium oxide with microporous bioceramics on biocompatible metals/ceramics such as $Al_2O_3$, $ZrO_2$ and Ti with or without delivery of therapeutic molecules for local healing or accelerated cell recovery of bone.

EXPERIMENTAL PART

I—MATERIALS AND METHODS

Hydroxyapatite: a 99.99% pure hydroxyapatite (formula $Ca_{10}(PO4)_6(OH)_2$) with a particle size of 15-25 nm was used, marketed by American Elements under the name Hydroxyapatite nanopowders.

Gelatin: a gelatin marketed by Sigma Aldrich under the name Gelatin Solution type B, 2% was used.

Collagen: a collagen marketed by Sigma Aldrich under the name Collagen, type 1 solution from rat tail BioReagent was used.

Cross-linking agent: Glutaraldehyde solution Grade I, 25% in $H_2O$, marketed by Sigma Aldrich was used.

Alumina: a 99% pure alumina (formula $Al_2O_3$) with a particle size of 20 nm was used, marketed by US-Nano under the name $Al_2O_3$.

Titanium dioxide: a 99.7% pure titanium dioxide (formula $TiO_2$) with a particle size of 25-100 nm in anatase or rutile form was used, marketed by Sigma Aldrich.

Zirconium dioxide: a 99.9999% pure zirconia (formula $ZrO_2$) with a particle size of 20-40 nm and a (3YSZ) or (8YSZ) structure was used.

Tube: the flexible tube is made from 1 mm-thick silicone and is marketed by MacoPharma.

Isostatic press: constituted by a High Pressure section: HP chamber (ICMCB) containing the sample and silicone oil (pressure-transmitting fluid) and a hydropneumatic pump (NovaSwiss) making it possible to compress the fluid and a second Low Temperature section: vessel in which the HP chamber containing the silicone oil refrigerated with an immersion cooler (Huber) is placed.

Mechanical strength: mechanical strength is evaluated initially by a manual strength test. The mechanical strength is deemed satisfactory if the material can be handled without deterioration.

Porosity examination: the porosity is measured by scanning electron microscopy (SEM).

II—EXAMPLES

II.1. Preparation of the Suspension

Product suspensions are prepared with the components and proportions described in tables 1.1 to 1.4 below.

1 g of mineral material is introduced into a mixer optionally in the presence of additives and with different quantities of water depending on the quantity of porosity required, to prepare a suspension by mixing homogeneously. Tables 1.1 to 1.4 give the percentages by weight (Wt %) of each material.

In the case of tables 1.2 and 1.3 two steps were performed. In a first step, the HAp+Additive were mixed, utilising HAp and the additive (gelatin or collagen) in the ratios given in the corresponding columns. In a second step, the quantity of water given in the right-hand column was added to this first mixture so as to reach a total of 100%.

Example 1.1: Porous Pure Hydroxyapatite (HAp)

TABLE 1.1

|  | HAp Wt % | Water Wt % |
|---|---|---|
| Example 1.1 a | 90 | 10 |
| Example 1.1 b | 80 | 20 |
| Example 1.1 c | 70 | 30 |
| Example 1.1 d | 60 | 40 |

Example 1.2: Porous Hydroxyapatite (HAp) with Gelatin

TABLE 1.2

|  | Premix | | Water Wt % |
|---|---|---|---|
|  | HAp Wt % | Additive Wt % |  |
| Example 1.2 a | 65 | Gelatin 35% | 50 |
| Example 1.2 b | 65 | Gelatin 35% | 70 |
| Example 1.2 c | 65 | Gelatin 35% | 90 |
| Example 1.2 d | 85 | Gelatin 15% | 50 |
| Example 1.2 e | 85 | Gelatin 15% | 70 |
| Example 1.2 f | 85 | Gelatin 15% | 90 |

Example 1.3: Porous Hydroxyapatite (HAp) with Collagen

TABLE 1.3

|  | Premix | | Water Wt % |
|---|---|---|---|
|  | HAp Wt % | Additive Wt % |  |
| Example 1.3 a | 65 | Collagen 35% | 50 |
| Example 1.3 b | 65 | Collagen 35% | 70 |
| Example 1.3 c | 65 | Collagen 35% | 90 |
| Example 1.3 d | 85 | Collagen 15% | 50 |
| Example 1.3 e | 85 | Collagen 15% | 70 |
| Example 1.3 f | 85 | Collagen 15% | 90 |

Example 1.4: Various Materials

TABLE 1.4

|  | Material | % material | Water Wt % |
|---|---|---|---|
| Example 1.4 a | HAp | 80 wt % HAp | 20 |
| Example 1.4 b | $Al_2O_3$ | 60 wt % $Al_2O_3$ | 40 |
| Example 1.4 c | $TiO_2$ | 70 wt % $TiO_2$ | 30 |
| Example 1.4 d | 8YSZ | 70 wt % 8YSZ | 30 |
| Example 1.4 e | 3YSZ | 70 wt % 3YSZ | 30 |
| Example 1.4 f | $ZrO_2$ | 70 wt % $ZrO_2$ | 30 |

II.2 Treatment Cycle:

The 1 g suspension is transferred to a flexible tube that can withstand negative temperature and is placed in the isostatic press at T≈−6° C. to −20° C. The ice is formed in the suspension, which is subjected to various pressures (100 MPa-400 MPa) for different time periods to obtain a hard sample. The mechanical strength of the sample is varied depending on the dwell time and pressure cycle (pressure of the single-cycle/multiple-cycle step). After compression, the sample is then lyophilized to transform the water from the solid state to the gaseous state. Then, the sample is removed from the pouch; it has a porous structure and high mechanical strength. Optionally, the sample is immersed in a solution of cross-linking agent.

The treatment cycles to which the suspensions are subjected are described in detail in the tables below.

Cycle A

TABLE A

|  | Temperature | Pressure | Duration |
|---|---|---|---|
| Step 1 | −15° C., −5° C. | 1 MPa | 10 min, 20 min |
| Step 2 | −15° C., −5° C. | 100, 200, 300 MPa | 5 min, 10 min, 15 min |
| Step 3 | −15° C., −5° C. | 100, 200, 300 MPa | 5 min, 10 min, 15 min |
| Step 4 | −15° C., −5° C. | 1 MPa | 5 min |
| Step 5 | 0° C. | 0 MPa | 1 min |
| Step 6 (lyophilisation) | Ambient | 0 MPa | 2 hrs |

Cycle B

TABLE B

| | Temperature | Pressure | Duration | Immersion in a cross-linking agent |
|---|---|---|---|---|
| Step 1 | −15° C., −5° C. | 1 MPa | 10 min, 20 min | — |
| Step 2 | −15° C., −5° C. | 100, 200, 300 MPa | 5 min, 10 min, 15 min | — |
| Step 3 | −15° C., −5° C. | 100, 200, 300 MPa | 5 min, 10 min, 15 min | — |
| Step 4 | −15° C., −5° C. | 1 MPa | 5 min | — |
| Step 5 | 0° C. | 0 MPa | 1 min | — |
| Step 6 (lyophilisation) | Ambient | 0 MPa | 2 hrs | — |
| Step 7 | Ambient | 0 MPa | 1 min | Yes |

II.3 Results:

The following materials were prepared starting from the suspensions described above and applying the treatment cycles described above; the treatment conditions of each sample are summarised in tables 3.1 to 3.4, together with the properties of the products obtained:

Example 3.1: Porous Pure Hydroxyapatite (HAp)

TABLE 3.1

| Suspension | Cycle | Observation | Porosity |
|---|---|---|---|
| Example 1.1 a | A | rigid | ≤65% |
| Example 1.1 b | A | rigid | ≤55% |
| Example 1.1 c | A | rigid | ≤45%, |
| Example 1.1 d | A | rigid | ≤35% |

Example 3.2: Porous Hydroxyapatite (HAp) with Gelatin

TABLE 3.2

| Suspension | Cycle | Observation | Porosity |
|---|---|---|---|
| Example 1.2 a | B | rigid | ≤35% |
| Example 1.2 b | B | rigid | ≤45% |
| Example 1.2 c | B | rigid | ≤55% |
| Example 1.2 d | B | rigid | ≤35% |
| Example 1.2 e | B | rigid | ≤45% |
| Example 1.2 f | B | rigid | ≤55% |

Example 3.3: Porous Hydroxyapatite (HAp) with Collagen

TABLE 3.3

| Suspension | Cycle | Observation | Porosity |
|---|---|---|---|
| Example 1.3 a | B | rigid | ≤35% |
| Example 1.3 b | B | rigid | ≤45% |
| Example 1.3 c | B | rigid | ≤55% |
| Example 1.3 d | B | rigid | ≤35% |
| Example 1.3 e | B | rigid | ≤45% |
| Example 1.3 f | B | rigid | ≤55% |

Example 3.4: Various Materials

TABLE 3.4

| Suspension | Cycle | Observation | Porosity |
|---|---|---|---|
| Example 1.4 a | A | Rigid | 55% |
| Example 1.4 b | A | Rigid | 65% |
| Example 1.4 c | A | Rigid | 65% |
| Example 1.4 d | A | Rigid | 35% |
| Example 1.4 e | A | Rigid | 30% |
| Example 1.4 f | A | Rigid | 20% |

The structure of the materials was observed by means of a Scios Dual Beam device, FEI, France. FIB-SEM microscopy and STEM-EDS electronic tomography were carried out on the sample of example 1.1 b. The observations were made so as to allow the quantification of the morphological and geometric spatial distributions of the multi-scale porous network at scales of length ranging from a few tens of microns to less than one nanometre. The microstructure was analysed in high vacuum at a voltage of 2 kV. The photos show a homogeneous distribution of porosity in the monolith produced by the method of the invention.

The invention claimed is:

1. Method for producing a porous monolithic material (5), this method comprising at least the following steps:
    (a) Supplying at least one mineral or organic powder (S),
    (b) Preparing a mixture (1) comprising at least the powder of step (a) and at least one solvent,
    (c) Packing the mixture of step (b) in sealed packaging (2) made from an elastically deformable material in order to form a sample (3),
    (d) Applying to the sample (3) of step (c) a pressure (P) greater than or equal to 50 MPa at a temperature at which the solvent is in solid form,
    (e) Returning to atmospheric pressure,
    (f) Opening the packaging and recovering the material,
    (g) Removing the solvent at a temperature at which the solvent is in solid form.

2. Method according to claim 1, in which the powder (S) is selected from mineral or inorganic powders.

3. The method of claim 2, wherein the powder (S) is selected from: metals, their salts and derivatives, chosen from oxides, hydroxides, phosphate salts, carbonate salts, borides, carbides, and nitrides; ceramics; and composite materials.

4. Method according to claim 2, in which the mixture (1) of step (b) comprises at least one organic component.

5. Method according to claim 2, in which the mixture (1) comprises 50 to 95% by weight of powder (S) with respect to the total weight of the mixture.

6. The method of claim 3, wherein the powder (S) is selected from alkali and alkaline earth metals and transition metals.

7. Method according to claim 1 in which the powder (S) is mineral or inorganic and is selected from: hydroxyapatite, alumina, titanium dioxide, zirconia, Yttria-Stabilized Zirconia (YSZ) and Magnesia Partially Stabilized Zirconia (PSZ).

8. Method according to claim 7, in which the mixture (1) of step (b) comprises at least one organic component.

9. Method according to claim 1, in which the mixture (1) of step (b) comprises at least one organic component.

10. The method of claim 9, wherein the at least one organic component is selected from a group consisting of: a therapeutic active ingredient; peptides; proteins; coagulants; markers; growth factors; natural or synthetic polymers; dopants for electronics; electrically conductive polymers; chemical sensors; a cross-linking agent; and a water-miscible solvent.

11. Method according to claim 1, in which the mixture (1) comprises 50 to 95% by weight of powder (S) with respect to the total weight of the mixture.

12. The method of claim 11, wherein the powder (S) is mineral or inorganic powder.

13. Method according to claim 1, in which step (d) comprises at least the following sub-steps:
 (d1) Conditioning the sample at atmospheric pressure and at a temperature selected so that the solvent is in solid form,
 (d2) Applying a pressure greater than or equal to 50 MPa at a temperature selected so that the solvent is in solid form.

14. The method of claim 13, wherein the solvent is water.

15. Method according to claim 1, in which step (d) comprises at least conditioning at a temperature of between $-5°$ C. and $-60°$ C. and at a pressure of between 50 MPa and 700 MPa.

16. Method according to claim 1, in which the solvent is water and the removal of the water in step (g) is carried out by lyophilisation.

17. The method of claim 1, wherein the at least one solvent is water.

* * * * *